(12) United States Patent
Pandey et al.

(10) Patent No.: US 9,108,972 B2
(45) Date of Patent: Aug. 18, 2015

(54) SALTS OF DPP-IV INHIBITOR

(75) Inventors: Bipin Pandey, Gujarat (IN); Mayank Ghanshyambhai Dave, Gujarat (IN); Himanshu M. Kothari, Gujarat (IN); Bhavin Shriprasad Shukla, Gujarat (IN)

(73) Assignee: Cadila Healthcare Limited, Ahmedabad, Gujarat (IN)

( * ) Notice: Subject to any disclaimer, the term of this patent is extended or adjusted under 35 U.S.C. 154(b) by 0 days.

(21) Appl. No.: 14/002,541

(22) PCT Filed: Mar. 2, 2012

(86) PCT No.: PCT/IN2012/000148
§ 371 (c)(1),
(2), (4) Date: Oct. 31, 2013

(87) PCT Pub. No.: WO2012/147092
PCT Pub. Date: Nov. 1, 2012

(65) Prior Publication Data
US 2014/0051856 A1    Feb. 20, 2014

(30) Foreign Application Priority Data

Mar. 3, 2011 (IN) .......................... 590/MUM/2011
Jul. 6, 2011 (IN) .......................... 1948MUM/2011
Sep. 30, 2011 (IN) .......................... 2777/MUM/2011

(51) Int. Cl.
C07D 487/04    (2006.01)
(52) U.S. Cl.
CPC .................................. C07D 487/04 (2013.01)
(58) Field of Classification Search
CPC .................................................... C07D 487/04
USPC ........................................................ 544/350
See application file for complete search history.

(56) References Cited

U.S. PATENT DOCUMENTS 6,699,871 B2 * 3/2004 Edmondson et al. ......... 514/249

FOREIGN PATENT DOCUMENTS

| EP | 2 019 113 | 1/2009 |
|---|---|---|
| WO | WO 03/004498 | 1/2003 |
| WO | WO 2005/072530 | 8/2005 |
| WO | WO 2009/085990 | 7/2009 |
| WO | WO 2010/004231 | 1/2010 |
| WO | WO 2010/117738 | 10/2010 |
| WO | WO 2013/001457 | 1/2013 |

OTHER PUBLICATIONS

West, Anthony R., Solid State Chemistry and Its Applications, Wiley, New York, 1988, 358.*
Stahl, et al., Handbook of Pharmaceutical Salts, Properties, Selection, and Use, Int'l Union of Pure and Applied Chemistry (IUPAC), Wiley-Vch (2002).*
International Search Report for PCT/IN2012/000148, mailed Jan. 31, 2013.
Anonymous, "Sitagliptin Salts, Processes for their Preparation and their use for the Preparation of Pharmaceutical Dosage Form", IP.com Journal, (Oct. 21, 2010), 88 pages.
Kim, B.H. et al., "Pharmacodynamic (Hemodynamic) and Pharmacokinetic Comparisons of S-Amlodipine Besylate in Healthy Korean Male Volunteers: Two Double-Blind, Randomized, Two-Period, Two-Treatment, Two-Sequence, Double-Dummy, Single-Dose Crossover Studies", Clinical Therapeutics, vol. 32, No. 1, (Jan. 1, 2010), pp. 193-205.
Lee, H.Y. et al., "Clinic Blood Pressure Responses to Two Amlodipine Salt Formulations, Adipate and Besylate, in Adult Korean Patients with Mild to Moderate Hypertension: A Multicenter, Randomized, Double-Blind, Parallel-Group, 8-Week Comparison", Clinical Therapeutics, vol. 27, No. 6 (Jun. 1, 2005), pp. 728-739.

* cited by examiner

*Primary Examiner* — Erich A Leeser
(74) *Attorney, Agent, or Firm* — Nixon & Vanderhye P.C.

(57) ABSTRACT

The present invention discloses new salts of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine i.e. gentisate, adipate and trifluoro acetic acid salts. The invention also describes the new. crystalline and amorphous forms of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine gentisate. The present invention also discloses novel crystalline salt form of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine hydrochloride and novel crystalline and amorphous salt forms of besylate and process for their preparation and isolation.

8 Claims, 10 Drawing Sheets

Figure: 9- Effect of single dose oral administration of ZY compounds at 10mg/kg, PO on OGTT in male C57 mice.
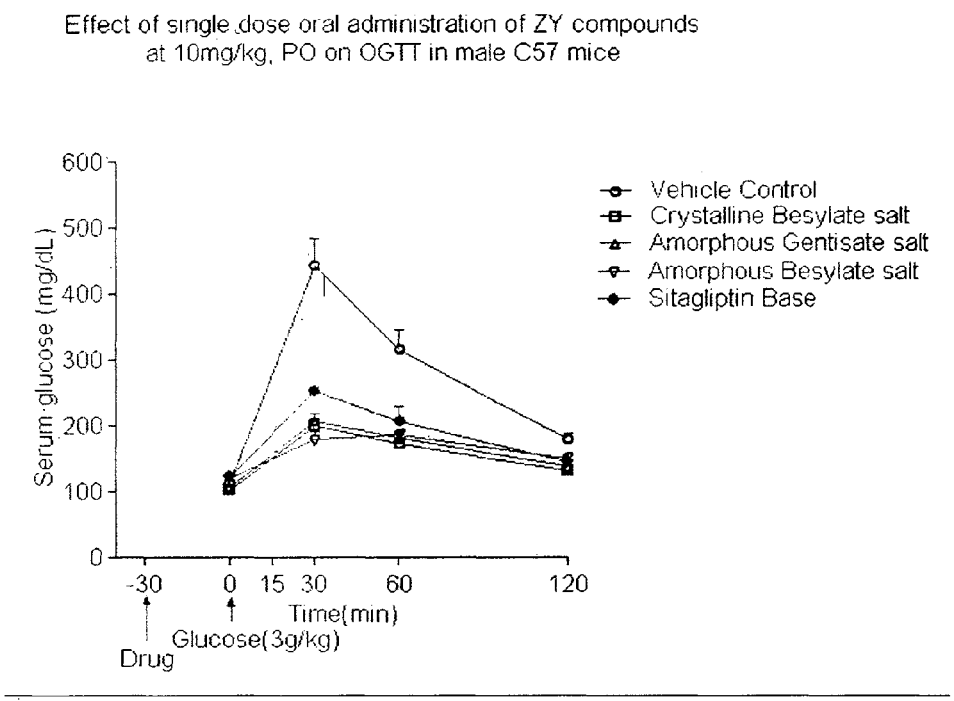

Figure: 10- Effect of single dose oral administration of ZY compounds at 10mg/kg, PO on OGTT in male C57 mice.
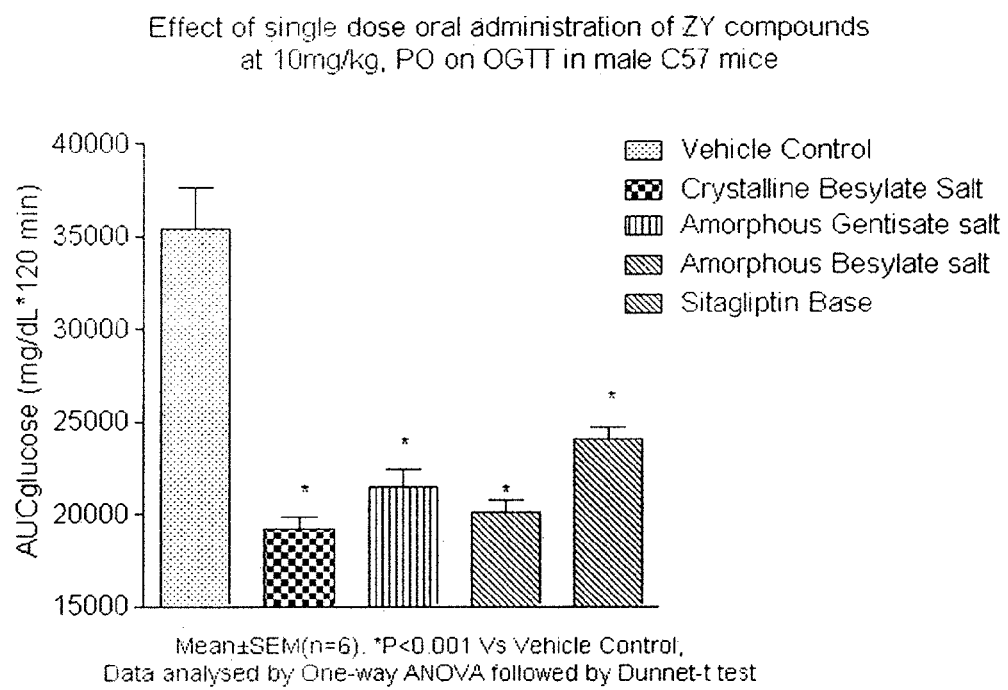

SALTS OF DPP-IV INHIBITOR

This application is the U.S. national phase of International Application No. PCT/IN2012/000148, filed 2 Mar. 2012, which designated the U.S. and claims priority to India Application No. 590/MUM/2011, filed 3 Mar. 2011; India Application No. 1948/MUM/2011, filed 6 Jul. 2011; and India Application No. 2777/MUM/2011, filed 30 Sep. 2011, the entire contents of each of which are hereby incorporated by reference.

FIELD OF INVENTION

The present invention discloses certain new salts of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine as well as their processes of preparation.

The present invention also discloses certain novel crystalline forms of (2R)-4-oxo-4-[3-(trifluoromethyl)-5,6-dihydro [1,2,4]-triazolo[4,3-a]pyrazin-7(8H)-yl]-1-(2,4,5-trifluorophenyl)butan-2-amine hydrochloride and novel crystalline and amorphous forms of the besylate salt and processes for their preparation and isolation.

BACKGROUND OF THE ART

The invention is related to novel salts and certain novel crystalline and amorphous forms of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine salts.

WO 03/004498 and U.S. Pat. No. 6,699,871 both assigned to Merck and Co., describes a class of beta-amino tetrahydrotriazolo[4,3-a]pyrazines, which are inhibitors of DPP-IV. Disclosed therein are compounds, whose general formula is,

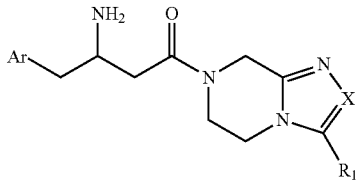

Specifically disclosed in WO 03/004498 is (2R)-4-oxo-4-[3-(trifluoromethyl)-5,6-dihydro[1,2,4]-triazolo[4,3-a] pyrazin-7(8H)-yl]-1-(2,4,5-trifluorophenyl)butan-2-amine. WO 03/004498 is silent as to the preparation of and the nature of specific crystal forms of the salts. WO 2005/003135 describes dihydrogenphosphate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine and crystalline hydrates thereof, in particular a crystalline monohydrate.

In WO 2005/003135 it is said that (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine dihydrogenphosphate salt and crystalline hydrates have advantages in the preparation of pharmaceutical compositions, such as ease of processing, handling, and dosing. In particular, they exhibit improved physical and chemical stability, such as stability to stress, high temperatures and humidity, as well as improved physicochemical properties, such as solubility and rate of dissolution. WO2005/020920 describes the crystalline anhydrate Form I, Form II and Form III as well as solvates of the (2R)-4-oxo-4-[3-(trifluoromethyl)-5,6-dihydro[1,2,4]-triazolo[4,3-a]pyrazin-7(8H)-yl]-1-(2,4,5-trifluorophenyl) butan-2-amine dihydrogenphosphate salt.

WO2005/030127 describes novel crystalline anhydrate Form IV of (2R)-4-oxo-4-[3-(trifluoromethyl)-5,6-dihydro [1,2,4]-triazolo[4,3-a]pyrazin-7(8H)-yl]-1-(2,4,5-trifluorophenyl)butan-2-amine dihydrogenphosphate salt.

WO2006/033848 describes the amorphous form of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine dihydrogenphosphate salt.

WO2005/072530 describes crystalline hydrochloric acid, benzenesulfonic acid, p-toluenesulfonic acid, 10-camphorsulfonic acid, and tartaric acid salts of (2R)-4-oxo-4-[3-(trifluoromethyl)-5,6-dihydro[1,2,4]-triazolo[4,3-a]pyrazin-7 (8H)-yl]-1-(2,4,5-trifluorophenyl)butan-2-amine and hydrates thereof.

WO2007/035198 describes (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine dodecylsulfate salt, in particular, a crystalline anhydrate form thereof.

In addition, the hemifumarate salt of (2R)-4-oxo-4-[3-(trifluoromethyl)-5,6-dihydro[1,2,4]-triazolo[4,3-a]pyrazin-7 (8H)-yl]-1-(2,4,5-trifluorophenyl)butan-2-amine has been described by D. Kim et al. in J. Med. Chem. 2005, 48, 141-151. Furthermore, International Patent Publication No. WO 2008/000418 discloses the preparation of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine hydrochloride in amorphous form.

In addition, International Patent Publication No. WO 2009/085990 describes other acid addition salts of (2R)-4-oxo-4-[3-(trifluoromethyl)-5,6-dihydro[1,2,4]-triazolo[4,3-a] pyrazin-7(8H)-yl]-1-(2,4,5-trifluorophenyl)butan-2-amine, including salts of di-p-tolyl-L-tartaric acid, phosphoric acid, sulfuric acid, hydrobromic acid, methanesulfonic acid, acetic acid, benzoic acid, oxalic acid, succinic acid, mandelic acid, fumaric acid, and lactic acid.

Patent Publication No. WO 2010/00469 describes different crystalline form of salts of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine such as hydrochloride, succinate, lactate, maleate, citrate and mesylate.

International Patent Publication No. WO 2010/092090 describes other acid addition salts of (2R)-4-oxo-4-[3-(trifluoromethyl)-5,6-dihydro[1,2,4]-triazolo[4,3-a]pyrazin-7 (8H)-yl]-1-(2,4,5-trifluorophenyl)butan-2-amine, i.e. salts of D-glucuronic acid, L-glucuronic acid, glutaric acid, lactic acid, L-mandelic acid, D-mandelic acid and sulfuric acid.

International Patent Publication No. WO 2010/012781 describes other acid addition salts of (2R)-4-oxo-4-[3-(trifluoromethyl)-5,6-dihydro[1,2,4]-triazolo[4,3-a]pyrazin-7 (8H)-yl]-1-(2,4,5-trifluorophenyl)butan-2-amine, i.e., salts of ethanedisulfonic acid, galactaric acid, thiocyanic acid, and glutaric acid.

International Patent Publication No. WO 2010/117738 disclosed different crystalline forms of acetate, oxalate and fumarate of compound of formula I. International Patent Publication No. WO 2012/007455 disclosed orotate salt of compound of formula I.

Different salts and new crystalline forms of the same pharmaceutically active moiety differ in their physical properties such as melting point, solubility, etc. These properties may appreciably influence pharmaceutical properties such as dissolution rate and bioavailability which in turn may have an impact on their efficacy. Thus there is a continuing need to obtain new salts of (2R)-4-oxo-4-[3-(trifluoromethyl)-5,6-dihydro[1,2,4]-triazolo[4,3-a]pyrazin-7(8H)-yl]-1-(2,4,5- trifluorophenyl)butan-2-amine having improved physical and/or chemical properties. The present invention satisfies this need by providing new salts of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

In view of the foregoing, it would be desirable to provide new crystalline forms of salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine. We herein disclose new salts i.e. (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine gentisate, (2R)-4-oxo-4-[3-(trifluoromethyl)-1-dihydro[1,2,4]-triazolo[4,3-a]pyrazin-7(8H)-yl]-1-(2,4,5-trifluorophenyl)butan-2-amine adipate and novel trifluoroacetic acid salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

We herein also disclose new crystalline salt form of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine hydrochloride and new crystalline and amorphous salt forms of besylate which have not been disclosed in prior art.

These salts and new crystalline salt forms can show certain superior pharmaceutical properties compared to (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

All of these salts may be present either in substantially crystalline or amorphous forms or may be present as partially crystalline forms.

In an embodiment, the present invention provide new salts and new crystalline salt forms of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine which can be used as an intermediate to prepare pure (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine and/or pure (2R)-4-oxo-4-[3-(trifluoromethyl)-5,6-dihydro[1,2,4]-triazolo[4,3-a]pyrazin-7(8H)-yl]-1-(2,4,5-trifluorophenyl) butan-2-amine phosphate. Further, new salts and new crystalline salt forms of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine have desired physicochemical properties such as improved stability and/or solubility. This compound also shows superior efficacy over the (2R)-4-oxo-4-[3-(trifluoromethyl)-5,6-dihydro[1,2,4]-triazolo[4,3-a]pyrazin-7(8H)-yl]-1-(2,4,5-trifluorophenyl) butan-2-amine from which it is derived.

BRIEF DESCRIPTION OF THE DRAWINGS

FIG. 9—Effect of single dose oral administration of ZY compounds at 10 mg/kg, PO on OGTT in male C57 mice.

FIG. 10—Effect of single dose oral administration of ZY compounds at 10 mg/kg, PO on OGTT in male C57 mice.

OBJECT OF THE INVENTION

Figure 1:
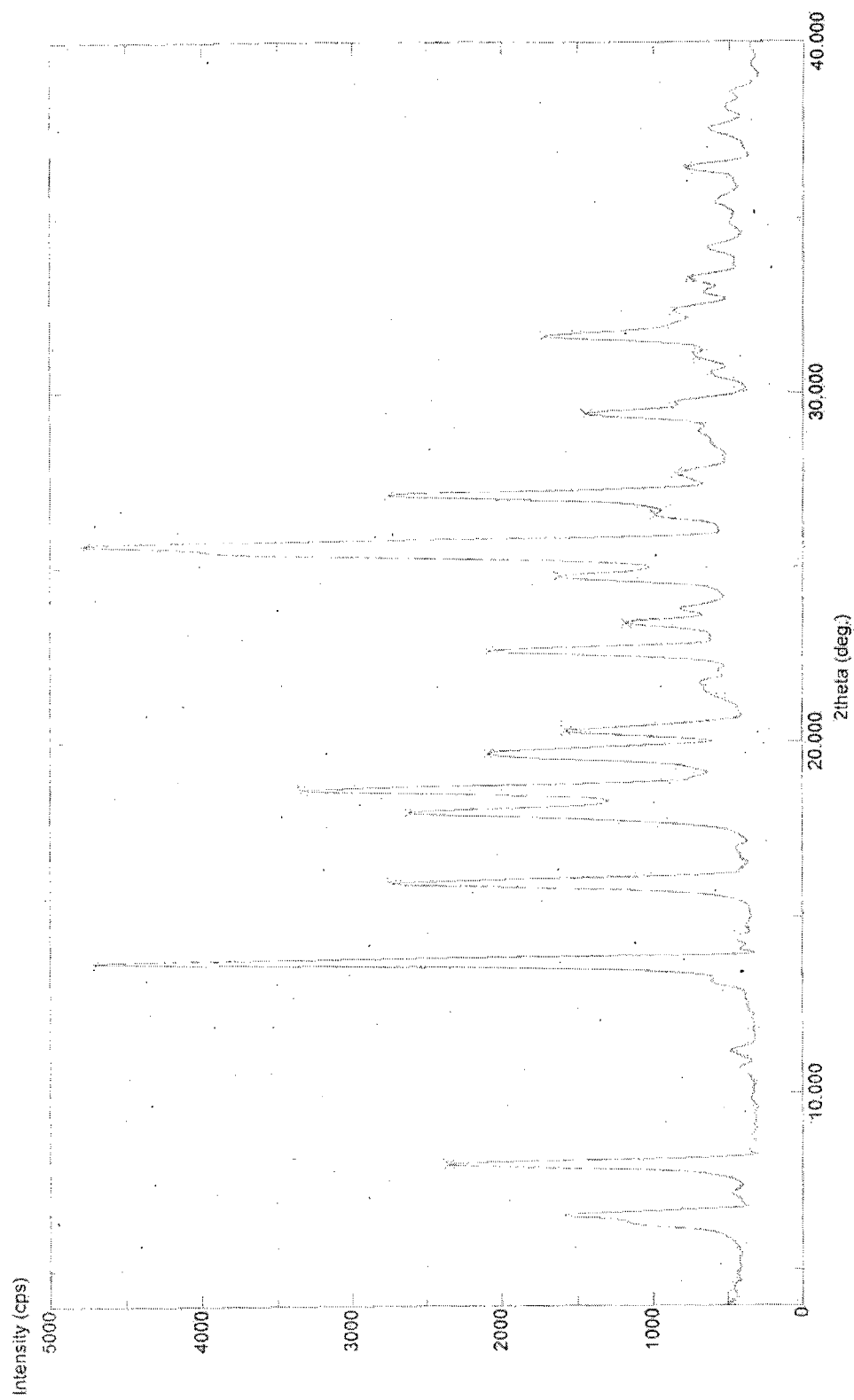
FIG. 1 is a powder X-ray diffraction (XRPD) pattern of crystalline gentisate salt of 2(R)4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention.

In an embodiment the present invention provides gentisate salt of (2R)-4-oxo-4-[3-(trifluoromethyl)-5,6-dihydro[1,2,4] triazolo[4,3-a]pyrazin-7(8H)-yl]-1-(2,4,5-trifluorophenyl) butan-2-amine and processes for their preparation.

In a preferred embodiment the present invention provides a crystalline form of gentisate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, which can be characterized by its powder X-ray diffraction (PXRD) pattern and other characteristic properties as described hereinafter and process of preparation thereof.

In another preferred embodiment the present invention provides the amorphous form of the gentisate salt of 4-oxo-4-[3-(trifluoromethyl)-5,6-dihydro[1,2,4]triazolo[4,3-a] pyrazin-7(8H)-yl]-1-(2,4,5-trifluorophenyl)butan-2-amine, which can be characterized by its powder X-ray diffraction (PXRD) pattern and other characteristic properties as described hereinafter and process for preparation thereof.

In an embodiment the present invention provides an adipate salt of (2R)-4-oxo-4-[3-(trifluoromethyl)-5,6-dihydro [1,2,4]triazolo[4,3-a]pyrazin-7(8H)-yl]-1-(2,4,5-trifluorophenyl)butan-2-amine and processes for their preparation.

In an embodiment the present invention provides a novel trifluoroacetic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine and processes for its preparation.

In an embodiment the present invention provides a new crystalline form of the hydrochloride salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, which can be characterized by its powder X-ray diffraction (PXRD) pattern and other characteristic properties as described hereinafter and process for preparation thereof.

In an embodiment the present invention provides a new crystalline besylate salt(I) of (2R)-4-oxo-4-[3-(trifluoromethyl)-5,6-dihydro[1,2,4]triazolo[4,3-a]pyrazin-7(8H)-yl]-

1-(2,4,5-trifluorophenyl)butan-2-amine, which can be characterized by its powder X-ray diffraction (PXRD) pattern and other characteristic properties as described hereinafter and process for preparation thereof.

In an embodiment the present invention provides a new crystalline besylate salt(II) of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, which can be characterized by its powder X-ray diffraction (PXRD) pattern and other characteristic properties as described hereinafter and process for preparation thereof.

In an embodiment the present invention provides an amorphous form of besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, which can be characterized by its powder X-ray diffraction (PXRD) pattern and other characteristic properties as described hereinafter and process for preparation thereof.

In a still further embodiment is provided a process for preparation of chemically and chirally pure (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine base through the intermediate formation of above disclosed novel salts and new crystalline salt forms.

DETAILED DESCRIPTION OF THE INVENTION

As used herein, the term "reflux temperature" refers to the boiling point of the solvent used.

As used herein, the term "PXRD" refers to powder X-ray diffraction.

As used herein, the term "(2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine refers to Sitagliptin.

As used herein, the term "THF" refers to tetrahydrofuran, the term "DCM" refers to dichloro methane, the term "DIPE" refers to di-isopropyl ether, the term "MTBE" refers to methyl t-butyl ether, the term "IPA" refers to isopropyl alcohol, the term "IPAc" refers to isopropyl acetatel, the term "phosphate" refers to dihydrogen phosphate salt, the term "besylate" refers to benzenesulphonic acid salt (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine is having structural formula (I).

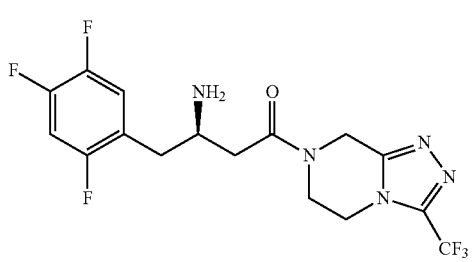

(I)

In one of the embodiment the invention discloses novel gentisate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

In an embodiment this salt may be present either in crystalline or amorphous form or suitable mixtures of crystalline and amorphous forms. In a further embodiment, the crystalline and/or amorphous forms may exist either in hydrated, solvated as well as non-solvated forms.

Hydrates of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine required for the preparation of crystalline (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine gentisate can be synthesized by process as mentioned in Example 17.

The terms 'dissolving', 'contacting', 'slurring', 'stirring', 'mixing' are interchangeable terms and doesn't affect the scope of the present invention.

In another embodiment, the invention provides a process for the synthesis of gentisate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine which comprises
(a) dissolving of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in a suitable solvent;
(b) thereafter addition of gentisic acid and reacting under suitable conditions and;
(c) removing the solvent under suitable conditions to obtain (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate.

The suitable solvents used may be selected from alcohols such as methanol, ethanol, isopropanol, butanol, 1,2-dimethoxy ethanol, 2-methoxy ethanol, 2-ethoxy ethanol, ethylene glycol and the like, water and suitable mixtures of one or more of the solvents described above.

In another embodiment, the (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine gentisic acid salt of the present invention can be prepared by reacting a (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine salt of a first acid with a gentisic acid, provided that the gentisic acid is stronger and sets free the first, weaker acid.

Another aspect, of the present invention provides for the new gentisate salt of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in a crystalline form.

The crystalline form of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate salt have a characteristic XRD peaks at about 8.0, 13.73, 16.00, 18.66, 22.61, 25.62 and 26.48°±0.2 degrees 2θ.

The crystalline form is further characterized by an additional XPRD peaks at about 6.53, 18.02, 19.68, 20.32, 23.40, 24.73, 27.05, 27.68, 29.38°±0.2° degrees 2θ. FIG. 1 illustrate the XRD of the crystalline form of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate salt.

In another embodiment, the invention provides a process for the synthesis of crystalline (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate salt, said process comprising crystallization of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate salt in the presence of suitable solvent and optionally further adding suitable anti solvents and subsequently removing the solvent, when necessary.

The suitable solvents used may be selected from alcohols such as methanol, ethanol, isopropanol, butanol, 1,2-dimethoxy ethanol, 2-methoxy ethanol, 2-ethoxy ethanol, ethylene glycol and the like; hydrocarbons such as hexane, heptanes, cyclohexane, toluene, xylene, chlorobenzene and the like and suitable mixtures of one or more of the solvents described above. Preferably a mixture of alcohol and hydrocarbon.

Another aspect of the present invention includes the new gentisate salt of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in amorphous form.

Anhydrous (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine required for the preparation of amorphous (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine gentisate, can be prepared by processes as mentioned in Example 18 and 19.

Figure 2:
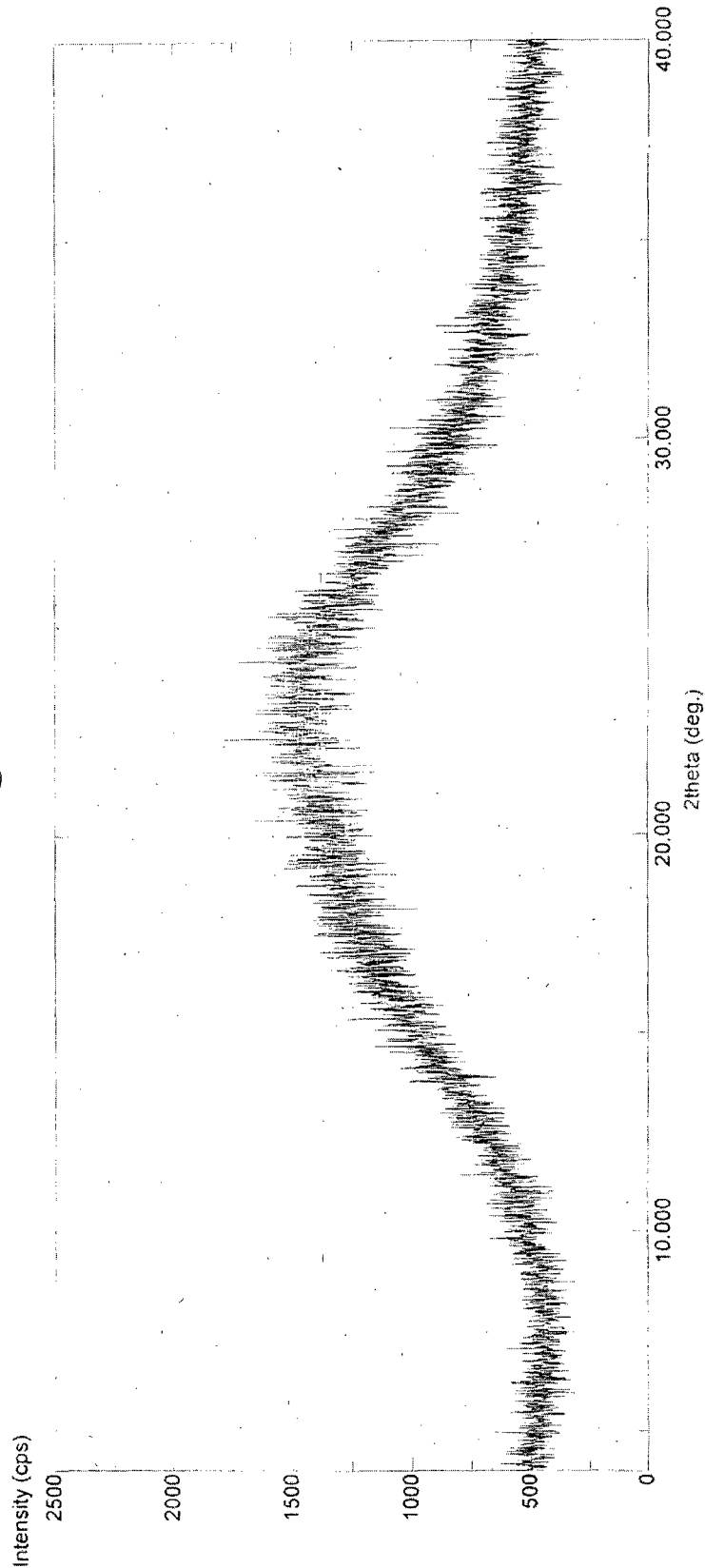
FIG. 2 is a powder X-ray diffraction (XRPD) pattern of amorphous gentisate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention

FIG. 2 illustrate the XRD of an amorphous form of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate salt.

In another embodiment, the invention provides a process for the synthesis of the amorphous form of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine gentisate salt, said process comprising reaction of the free base with the gentisic acid in suitable solvent under suitable conditions and optionally adding suitable anti solvents and removing the solvent when necessary.

The suitable solvents used may be selected from alcohols such as methanol, ethanol, isopropanol, butanol, 1,2-dimethoxy ethanol, 2-methoxy ethanol, 2-ethoxy ethanol, ethylene glycol and the like and water and suitable mixtures of one or more of the solvents described above to prepare gentisate salt.

In another embodiment, the invention provides a process for the synthesis of amorphous (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine gentisate salt, said process comprising dissolving or slurring of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate salt in the presence of suitable solvent and optionally further adding suitable anti solvents and subsequently removing the solvent, when necessary.

The suitable solvents used may be selected from alcohols such as methanol, ethanol, isopropanol, butanol, 1,2-dimethoxy ethanol, 2-methoxy ethanol, 2-ethoxy ethanol, ethylene glycol and the like; esters such as ethyl acetate, isopropyl acetate and the like; chlorinated solvents such as chloroform, dichloromethane and the like; nitriles such as acetonitrile and the like; ethers such as diethyl ether, 1,4-dioxane, DIPE, MTBE, THF and the like and suitable mixtures of one or more of the solvents described above.

In one of the embodiment the invention discloses novel adipate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

In an embodiment this salt may be present either in crystalline or amorphous form or suitable mixtures of crystalline and amorphous forms. In a further embodiment, the crystalline and/or amorphous forms may exist either in hydrated, solvated as well as non-solvated forms.

Hydrates of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine required for the preparation of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine adipate, can be synthesized by process as mentioned in Example 17.

In another embodiment, the invention provides a process for the synthesis of the adipate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

Adipate salts may be prepared by reaction of the free base (formula I) under suitable reaction conditions with the adipic acid in water or one or more suitable organic solvents or in a mixture of water and one or more suitable organic solvents and removing the solvent when necessary.

The suitable solvents used may be selected from alcohols such as methanol, ethanol, isopropanol, butanol, 1,2-dimethoxy ethanol, 2-methoxy ethanol, 2-ethoxy ethanol, ethylene glycol and the like and suitable mixtures thereof.

Furthermore, the (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine adipate salts of the present invention can be prepared by reacting a (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine salt of a first acid with adipic acid, provided that the adipic acid is stronger and sets free the first, weaker acid.

The crystalline form of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine adipate salt is having a characteristic XRD peaks at about 8.05, 17.64, 18.29, 21.65, 23.38, 23.85 and 24.38°±0.2 degrees 2θ.

The crystalline form is further characterized by an additional XPRD peaks at about 5.98, 10.03, 13.78, 15.72, 16.15, 22.34, 22.85, 25.09, 25.45 and 29.43°±0.2° degrees 2θ.

Figure 3:
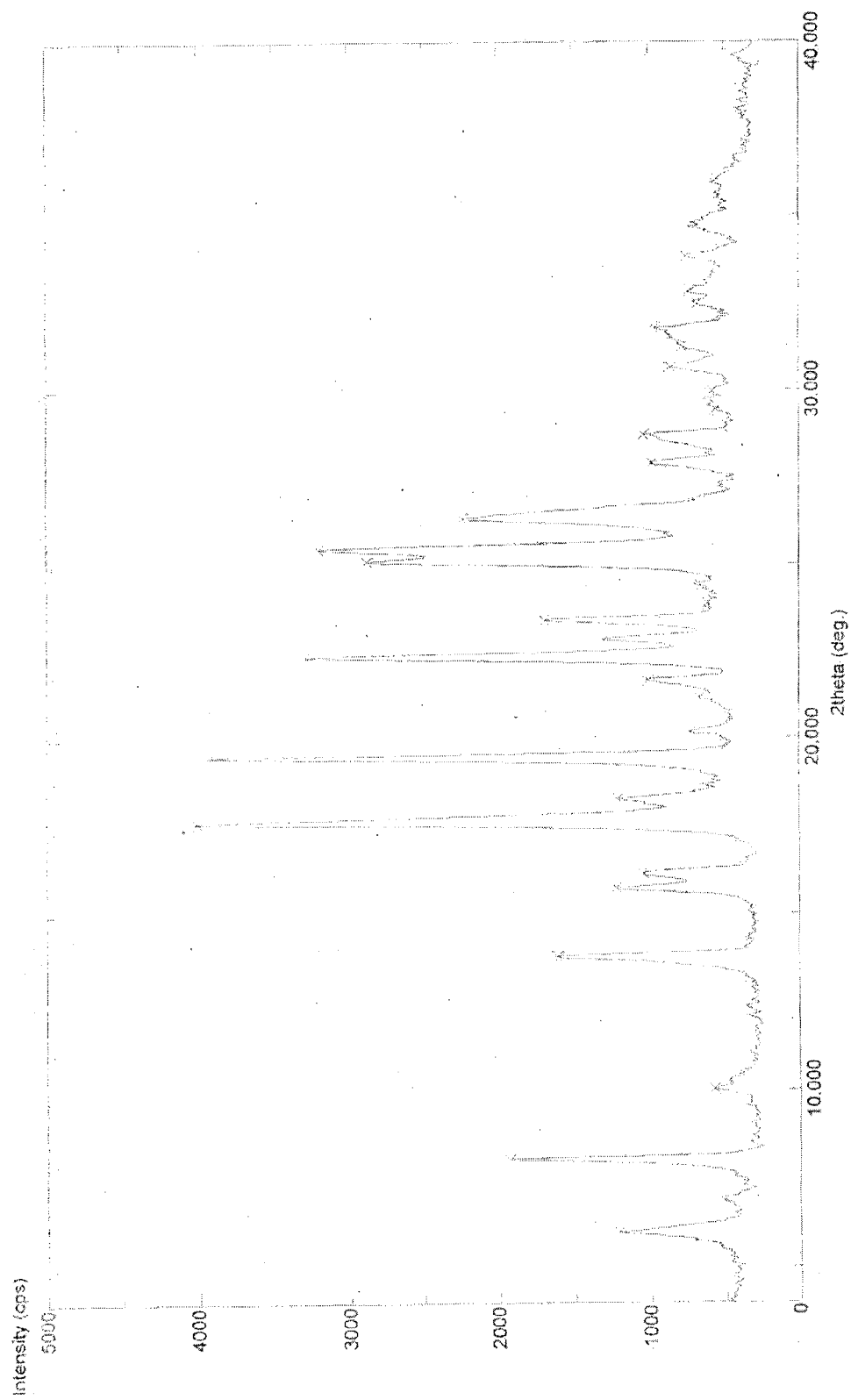
FIG. 3 is a powder X-ray diffraction (XRPD) pattern of crystalline adipate salt of 2(R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention.

FIG. 3 illustrate the XRD of a crystalline form of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine adipate salt.

In one of the embodiments, the invention discloses novel trifluoro acetic acid salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

In an embodiment this salt may be present either in crystalline or amorphous form or suitable mixtures of crystalline and amorphous forms. In a further embodiment, the crystalline and/or amorphous forms may exist either in hydrated, solvated as well as non-solvated forms.

Anhydrous (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine required for the preparation of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine trifluoro acetic acid salt, can be synthesized by processes as mentioned in Examples 18 and 19 of this specification.

In another embodiment, the invention provides a process for the synthesis of trifluoro acetic acid salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

Trifluoro acetic acid salts can be prepared by reaction of the free base (formula I) under suitable reaction conditions with the trifluoro acetic acid in water or one or more suitable organic solvents or in a mixture of water and one or more suitable organic solvents or mixture of suitable solvents and subsequently removing water or the solvent used, under suitable conditions when necessary.

The suitable solvents used may be selected from alcohols such as methanol, ethanol, isopropanol, butanol, 1,2-dimethoxy ethanol, 2-methoxy ethanol, 2-ethoxy ethanol, ethylene glycol and the like and suitable mixtures of one or more of the solvents described above. In another embodiment, the (2R)-4-oxo-4-[3-(trifluoromethyl)-5,6-dihydro[1, 2,4]-triazolo[4,3-a]pyrazin-7(8H)-yl]-1-(2,4,5-trifluorophenyl)butan-2-amine trifluoro acetic acid salt of the present invention can be prepared by reacting a (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine salt of a first acid with a trifluoro acetic acid, provided that the trifluoro acetic acid is stronger and sets free the first, weaker acid.

Suitable weaker acid salt of first acid is selected from HCl, acetic acid.

Another aspect of the present invention provides for the new trifluoroacetic acid salt of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in a crystalline form.

The crystalline form of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine trifluoroacetic acid salt have a characteristic XRD peaks at about 6.64, 9.39, 10.99, 13.40, 15.32, 17.15, 19.20, 19.66, 21.48, 22.46, 24.68, 26.89, 27.86, 29.34, 31.24, 32.77 and 34.82°±0.2 degrees 2θ.

Figure 6:
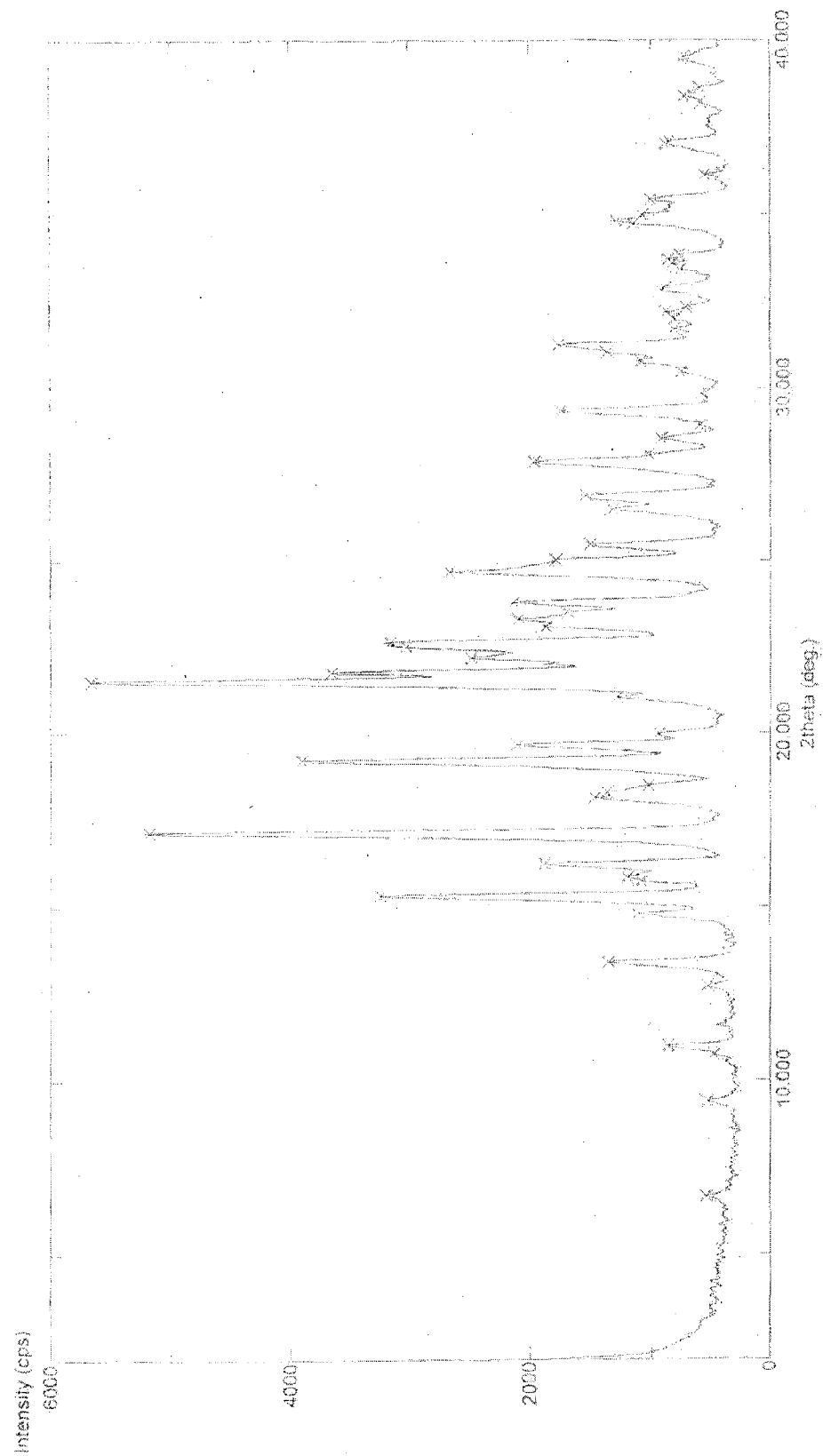
FIG. 6 is a powder X-ray diffraction (XRPD) pattern of crystalline trifluoroacetic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention.

FIG. 6 illustrate the XRD of crystalline form of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine trifluoroacetic acid salt.

Another aspect of the invention relates to a process for the preparation of crystalline form of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine trifluoroacetic acid salt, said process comprising crystallization of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine trifluoro acetic acid salt in the presence of suitable solvent and optionally further adding suitable anti solvents and subsequently removing the solvent, when necessary. The suitable solvents used may be selected from alcohols such as methanol, ethanol, isopropanol, butanol, 1,2-dimethoxy ethanol, 2-methoxy ethanol, 2-ethoxy ethanol, ethylene glycol and the like; esters such as ethyl acetate, isopropyl acetate and the like; ethers such as diethyl ether, 1,4-dioxane, DIPE, MTBE, THF and the like and suitable mixtures of one or more of the solvents described above.

In an embodiment is provided a novel crystalline hydrochloride salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine.

Another aspect of the invention relates to a process for the preparation of a new crystalline hydrochloride salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

Anhydrous (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine required for the preparation of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine hydrochloride salt, can be synthesized by processes as mentioned in Example 18 and 19.

A new crystalline hydrochloride salt can be prepared by reaction of the free base (formula I) under suitable reaction conditions with the hydrochloric acid in water or one or more suitable organic solvents or in a mixture of water and one or more suitable organic solvents and removing the solvent under suitable conditions when necessary.

The suitable solvents used may be selected from alcohols such as methanol, ethanol, isopropanol, butanol, 1,2-dimethoxy ethanol, 2-methoxy ethanol, 2-ethoxy ethanol, ethylene glycol, hexanol, heptanol, octanol, decanol and the like; ethers such as diethyl ether, 1,4-dioxane, DIPE, MTBE, THF and the like and suitable mixtures of one or more of the solvents described above.

The crystal line form of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine hydrochloride salt have a characteristic XRD peaks at about 6.50, 8.05, 13.79, 18.05, 19.52, 22.65, 23.40, 25.39 and 27.09°±0.2 degrees 2θ.

The crystalline form is further characterized by an additional XPRD peaks at about 16.03, 18.71, 22.36, 24.79, 26.49±0.2° degrees 2θ.

Figure 4:
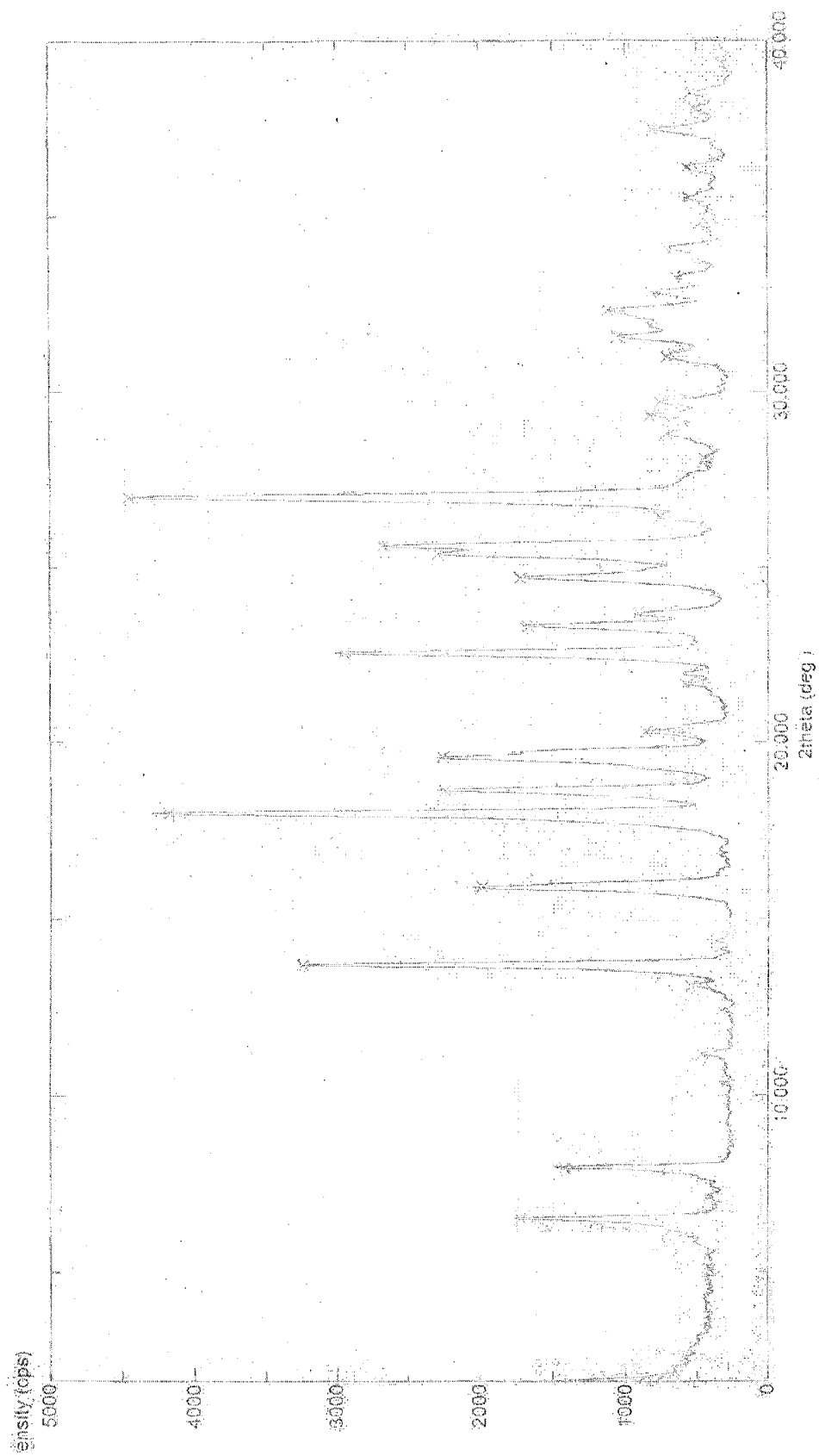
FIG. 4 is a powder X-ray diffraction (XRPD) pattern of crystalline hydrochloride salt of 2(R)4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention.

FIG. 4 illustrate the XRD of crystalline form of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine hydrochloride salt.

In one of the embodiment the invention discloses a novel crystalline form of besylate salt(I) of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

Anhydrous (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine required for the preparation of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine besylate salt(I), can be synthesized by processes as mentioned in Example 18 and 19.

Another aspect of the invention relates to a process for the preparation of a novel crystalline form of besylate salt(I) of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

A novel crystalline form of besylate salt(I) can be prepared by reaction of the free base (formula I) under suitable reaction conditions with the benzenesulfonic acid in one or more suitable organic solvents and removing the solvent when necessary.

The suitable solvents used may be selected from esters such as ethyl acetate, isopropyl acetate and the like; hydrocarbons such as hexane, heptanes, cyclohexane, toluene, xylene, chlorobenzene and the like and suitable mixtures of one or more of the solvents described above.

The crystalline form of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine besylate salt is having a characteristic XRD peaks at about 6.81, 18.31, 22.99, 23.70 and 25.75°±0.2 degrees 2θ.

The crystalline form is further characterized by an additional XPRD peaks at about 12.62, 17.05, 19.35, 22.13, 27.56°±0.2° degrees 2θ.

Figure 5:
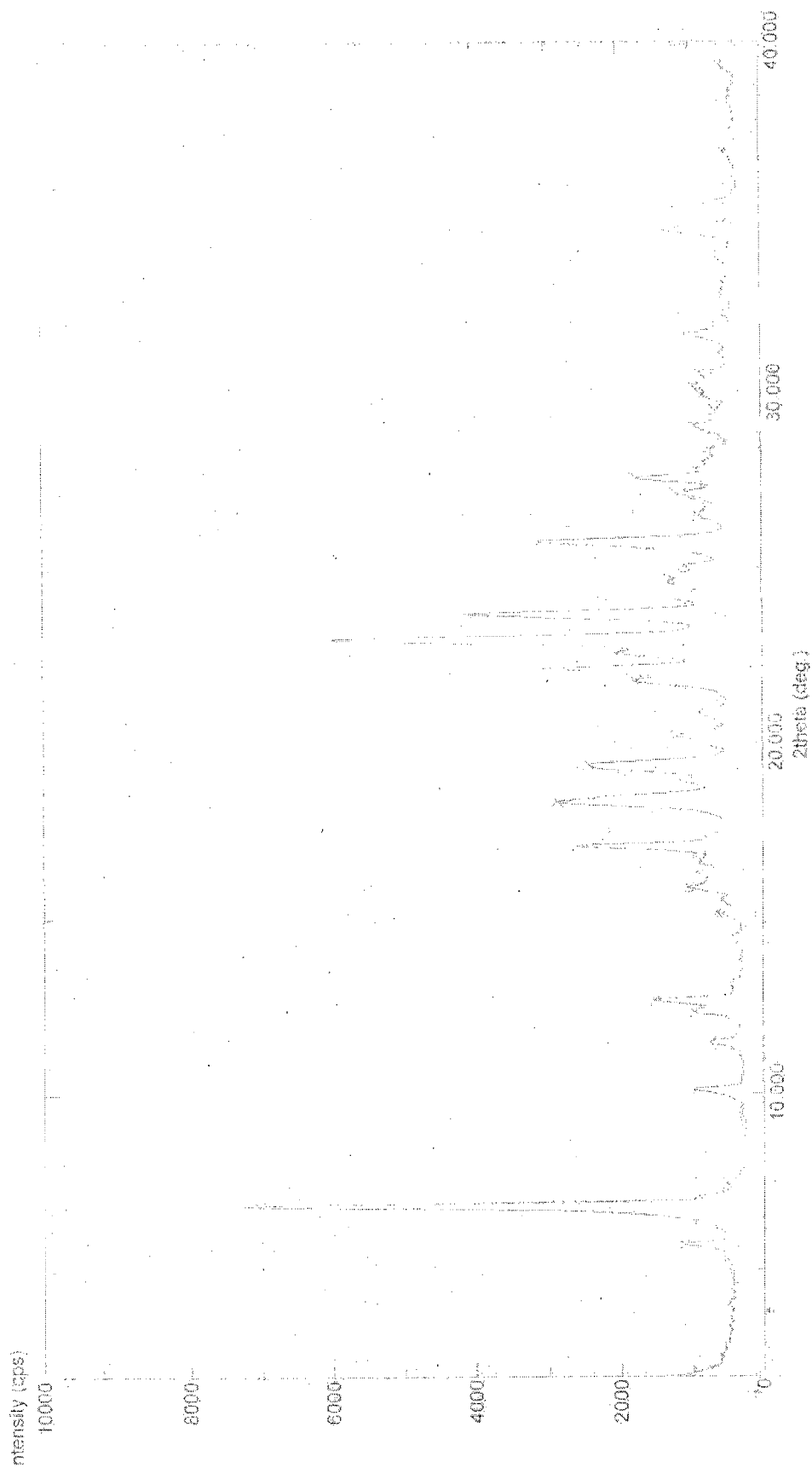
FIG. 5 is a powder X-ray diffraction (XRPD) pattern of crystalline besylate salt(I) of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention

FIG. 5 illustrate the XRD of crystalline form of 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine besylate(I) salt.

In an embodiment is provided a new crystalline form II of besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine and its hydrate.

Anhydrous (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine required for the preparation of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine besylate salt(II), can be synthesized by processes as mentioned in Example 18 and 19.

Another aspect of the invention relates to a process for the preparation of a new crystalline form II of besylate salt(II) of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

A new crystalline besylate salt(II) can be prepared by reaction of the free base under suitable reaction conditions with the benzenesulphonic acid in water or one or more suitable organic solvents or in a mixture of water and one or more suitable organic solvents or a suitable mixture of one or more organic solvents and subsequently removing the solvent under suitable conditions as are well known, when necessary.

The suitable solvents used may be selected from a mixture of esters and water, mixture of esters, ethers and water, mixture of esters, alcohols and water, mixture of ester, hydrocarbons, water and mixture of esters, ketones and water.

The suitable alcohols used is selected from methanol, ethanol, isopropanol, butanol, 1,2-dimethoxy ethanol, 2-methoxy ethanol, 2-ethoxy ethanol, ethylene glycol, hexanol, heptanol, octanol, decanol and the like; esters used is selected from ethyl acetate, isopropyl acetate and the like; chlorinated solvents used is selected from chloroform, dichloromethane and the like; hydrocarbons used is selected from hexane, heptanes, cyclohexane, toluene, xylene, chlorobenzene and the like; ketones used is selected from acetone and the like; ethers used is selected from diethyl ether, 1,4-dioxane, DIPE, MTBE, THF and the like.

The crystalline form II of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine besylate salt have a characteristic XRD peaks at about 5.69, 7.45, 10.08, 11.41, 13.09, 18.34, 22.52 and 22.97°±0.2 degrees 2θ.

The crystalline form II is further characterized by an additional XPRD peaks at about 16.63, 20.82, 21.95, 23.75, 24.49, 25.02, 26.43, 27.66 and 30.19±0.2° degrees 2θ.

Figure 7:
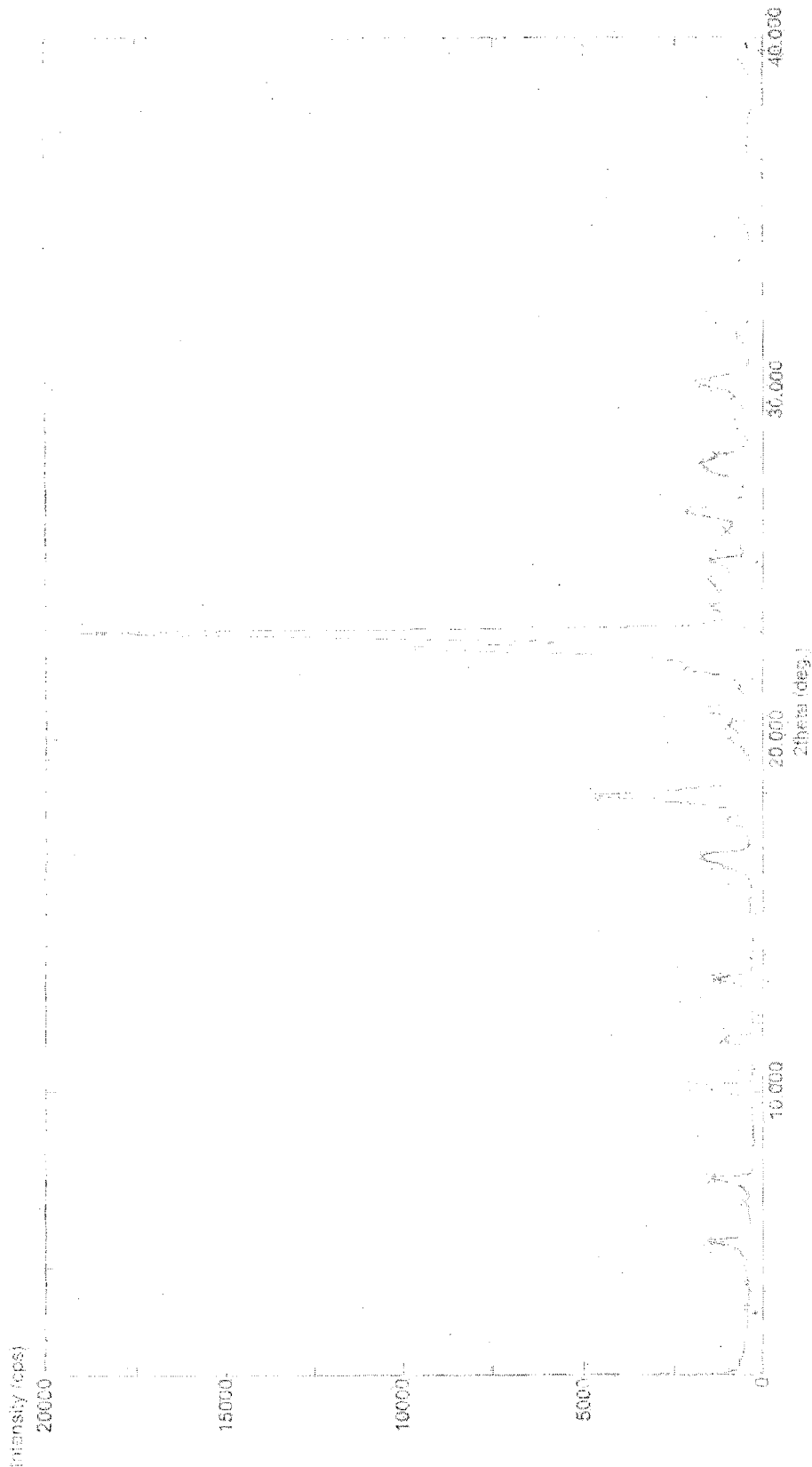
FIG. 7 is a powder X-ray diffraction (XRPD) pattern of crystalline besylate salt(II) of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention.

FIG. 7 illustrate the XRD of crystalline form II of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine besylate salt.

In other embodiments the present invention further includes substantially an amorphous form of besylate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine and processes to prepare the same.

Anhydrous (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine required for the preparation amorphous form of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine besylate salt, can be synthesized by processes as mentioned in example 18 and 19.

Substantially amorphous besylate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine in the present invention includes more than about 80%, more than about 90%, more than about 95%, or more than about 99%, by weight of amorphous content, the corresponding balance amount comprising of crystalline substances.

In an aspect, the present invention provides processes for the preparation of amorphous besylate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine, which comprises:

a) providing a solution of besylate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine in a suitable organic solvent; and b) recovering an amorphous form of besylate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine.

The step a) may involve dissolving the active substance in a solvent that is suitable for easy, commercially viable solvent removal via distillation, etc.

A solution of besylate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine may be obtained by dissolving besylate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine in suitable solvent, or by reacting (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine with benzene sulphonic acid, in a suitable solvent under suitable reaction conditions. The solvent that can be used for preparing amorphous besylate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine may be from the various classes of solvents such as for example alcohols, halogenated hydrocarbons, water or mixtures of any two or more thereof. Alcohol solvents include for example methanol, ethanol, denatured spirits, n-propanol, isopropanol, n-butanol, isobutanol, and t-butanol and the like. Halogenated hydrocarbons include for example dichloromethane, 1,2-dichloroethane, chloroform, carbon tetrachloride and the like.

This list is not intended to be exhaustive, and combinations of solvents that are useful can include more than one member of a class, and/or can be from different classes.

These and other classes of solvents known to a person skilled in the art are all contemplated without limitation. The organic solvent acceptable for the practice of the process described herein preferably provide sufficient solubility for the active substance, and do not cause any undesirable chemical reactions with the besylate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine, or (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine, such as degradation or side reaction, under the conditions of processing.

The recovering step b) may involve removing the solvent by distillation or by filteration.

It is generally preferred that rapid drying is utilized to provide the amorphous form of besylate salt of (2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine with desired stability, moisture content and residual solvent characteristics. The resultant product may be dried using any methods of drying including spray drying, rotational evaporation (such as using a Buchi Rotavapor), agitated thin film drying, spin-flash drying, fluid-bed drying, lyophilization, or other techniques known in the art.

The process may also include further drying of the product obtained from the solution by vacuum drying over a desiccant, such as phosphorous pentoxide ($P_2O_5$). The product can also be obtained with other suitable drying agents such as potassium carbonate ($K_2CO_3$), sodium carbonate ($Na_2CO_3$), silica gel and the like, as will be apparent to the skilled artisan.

Figure 8:
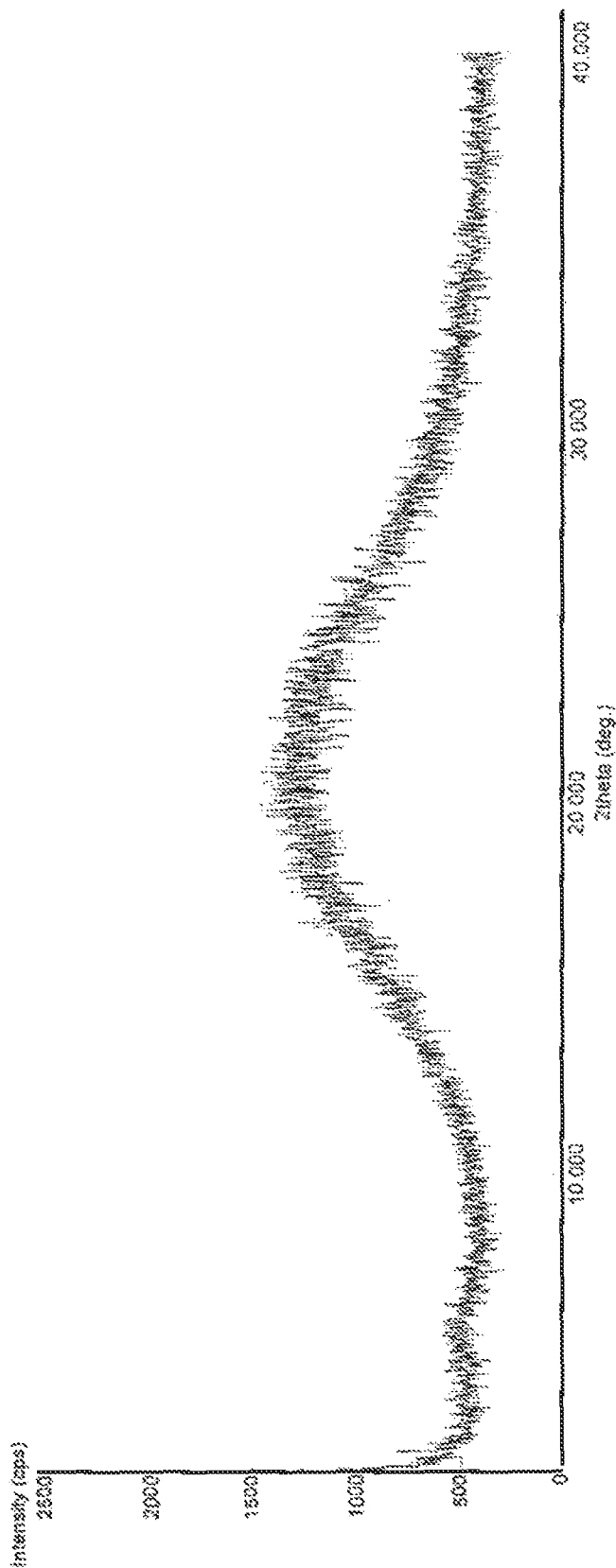
FIG. 8 is a powder X-ray diffraction (XRPD) pattern of amorphous besylate salt of 2(R)4-oxo-4-[3-(trifluoromethyl)-5,6-dihydro[1,2,4]triazolo[4,3-a]pyrazin-7(8H)-yl]-1-(2,4,5-trifluorophenyl)butan-2-amine according to the present invention.

FIG. 8 illustrates the XRD of an amorphous form of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine besylate salt.

Analytical Methods:

The complete x-ray powder spectrum, which was recorded with a Rigaku multifelx 2.0 Kilowatt X-ray powder diffractometer model using copper radiation. The X-ray diffraction pattern was recorded by keeping the instrument parameters listed below:

i) X-ray: Cu/40 kv/30 mA, Diverging slit: 1°, Scattering slit: 1°, Receiving slit: 0.15 mm, Monochromator RS: 0.8 mm, Counter: Scintillation counters;
Scan mode: Continuous, Scan speed: 4.000 deg./min., Sampling width: 0.010°,
Scan axes: 2 theta vs CPS, Scan range: 4° to 40.0°, Theta offset: 0.000.

ii) Differential scanning calorimetric analysis was carried out in a DSC-60 model from Shimadzu (S/W: TA-60WS Aquisition version 2.1.0.0) by keeping following parameters,
Sample Size Approx. 1-2 mg, Sample Pans: Hermetic/Crimping Pans,
Start Temperature: 50° C., End Temperature: 300° C., Rate of Heating: 10° C./min., Purge Gas: Nitrogen, Flow rate: 20 ml/min iii) The infrared (IR) spectrum has been recorded on a Shimadzu FTIR-8400 model spectrophotometer, between 450 $cm^{-1}$ and 4000 $cm^{-1}$, with a resolution of 4 $cm^{-1}$ in a KBr pellet.

iv) (2R)-4-oxo-4-[3-(trifluoromethyl)-5,6-dihydro[1,2,4]-triazolo[4,3-a]pyrazin-7(8H)-yl]-1-(2,4,5-trifluorophenyl) butan-2-amine and its salts were analyzed for purity by analytical HPLC at λmax 210 nm using column YMC-C8, 250 mm×4.6 mm×4 mm or its equivalent on AGILENT 1100 series under the following conditions,
Detector: UV absorption photometer Wave length: 210 nm
Column temp.: 25° C.
Flow rate: 1.0 mL/min. Injection Vol.: 10 μL
Mobile Phase: 10 mM $KH_2PO_4$ (pH-6.8): Acetonitrile (55:45)

(2R)-4-oxo-4-[3-(trifluoromethyl)-5,6-dihydro[1,2,4]-triazolo[4,3-a]pyrazin-7(8H)-yl]-1-(2,4,5-trifluorophenyl)butan-2-amine and its salts were analyzed for chiral purity by HPLC at λmax 268 nm using column Chiral-Cel OJ-H, 250 mm×4.6 mm×5μ or its equivalent on Shimadzu LCVP model under the following conditions, Detector: UV absorption photometer Wave length: 268 nm
Column temp.: 35° C.
Flow rate: 0.8 mL/min. Injection Vol.: 10 μL
Mobile Phase: 0.1% diethyl amine in [n-Hexane:Ethanol (90:10)]

v) Melting points were taken on VEEGO make model VMP-D melting point apparatus and are uncorrected.

(2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine trifluoro acetic acid salt, crystalline form II and amorphous forms of besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine and crystalline form of (2R)-4-oxo-4-[3-(trifluoromethyl)-5,6-dihydro[1,2,4]triazolo[4,3-a]pyrazin-7(8H)-yl]-1-(2,4,5-trifluorophenyl) butan-2-amine hydrochloride salt may also be useful as a therapeutic agent for treatment of certain disorders.

(2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine trifluoro acetic acid salt, crystalline form II and amorphous forms of besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine and crystal line form of (2R)-4-oxo-4-[3-(trifluoromethyl)-5,6-dihydro[1,2,4]triazolo[4,3-a]pyrazin-7(8H)-yl]-1-(2,4,5-trifluorophenyl) butan-2-amine hydrochloride salt prepared according to the present invention has chemical and polymorphic stability on storage at 25° C.±2° C./60%±5% RH for 3 months. Results of the stability of, crystalline form II and amorphous forms of besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, crystalline form of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine hydrochloride salt and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine trifluoroacetate are shown in table 1.

TABLE 1

STABILITY STUDY ON STORAGE (25° C. ± 2° C./60% ± 5% RH)

| Salt | Test | | Initial | After 3 Month |
|---|---|---|---|---|
| besylate amorphous | Description | | white colored powder | white colored powder |
| | Purity (By HPLC) | | 99.41% | 99.52% |
| | Water (by KFR) | | 1.01% | 3.14% |
| | Polymorphism | XRD | amorphous pattern | No Change |
| besylate crystalline(II) | Description | | white colored powder | Off white colored powder |
| | Purity (By HPLC) | | 99.87% | 99.97% |
| | Water (by KFR) | | 2.77% | 2.90% |
| | Polymorphism | XRD | Crystalline pattern | No Change |
| Hydrochloride crystalline | Description | | white colored powder | white colored powder |
| | Purity (By HPLC) | | 99.82% | 99.91% |
| | Water (by KFR) | | 3.54% | 4.01% |
| | Polymorphism | XRD | Crystalline pattern | No Change |
| TFA salt | Description | | white colored powder | white colored powder |
| | Purity (By HPLC) | | 97.89% | 97.5% |
| | Water (by KFR) | | 2.77% | 3.45% |
| | Polymorphism | XRD | Crystalline pattern | No Change |

The novel gentisate and adipate salt of the present application have some pharmaceutical advantages over the free base in the preparation of pharmaceutical drug product because both the novel salts are very stable.

It is to be noted that WO03004498 does not provide any biological activity data of the (2R)-4-oxo-4-[3-(trifluoromethyl)-5,6-dihydro[1,2,4]triazolo[4,3-a]pyrazin-7(8H)-yl]-

1-(2,4,5-trifluorophenyl)butan-2-amine. (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate, the crystalline form II and amorphous forms of besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine of the present invention is derived from (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine, and therefore, we are providing comparison of the (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate, crystalline form II and amorphous forms of besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine with crystalline monohydrate form of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate salt and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine.

Comparative efficacy study of (i) (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate (ii) crystalline form of the besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (iiii) amorphous besylate salt of (2R)-4-oxo-4-[3-(trifluoromethyl)-5,6-dihydro[1,2,4]triazolo[4,3-]pyrazin-7(8H)-yl]-1-(2,4,5-trifluorophenyl)butan-2-amine and vs. crystalline monohydrate form of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate salt and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (SB)

Test Material Particulars:
(i) (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate (SG).
(ii) crystalline besylate salt(II) of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine ($SB_{II}$).
(iii) amorphous besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (SBa).
(iv) Crystalline monohydrate form of (2R)-4-oxo-4-[3-(trifluoromethyl)-5,61-dihydro[1,2,4]triazolo[4,3-a]pyrazin-7(8H)-yl]-1-(2,4,5-trifluorophenyl)butan-2-amine phosphate salt (SP).
(v) (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (SB):

Study Protocol:
Eight to ten weeks old male C57BLKS/J mice obtained from Animal Research Facility of Zydus Research Centre were used. The mice were allowed ad libitum access to chow and water. Animals were on a 12-hour light, 12-hour dark cycle. Protocol for use of animals for conducting this study has been reviewed and approved by Institutional Animal Ethics Committee (IAEC).

Oral glucose tolerance test (OGTT) was performed on these animals. The mice were deprived of food for 18 h and then drug or vehicles were administered with a glucose load (3 g/kg) by oral route. Blood (200 μL) samples were collected at 0, 30, 60, 120 and 240 min. Serum glucose concentrations were determined using commercially available kits purchased from RFCL (New Delhi, India) using spectrophotometric assay. The glucose values were then analyzed using GraphPad Prism version 5.04 for Windows; GraphPad Software, San Diego, Calif., USA. The area under the curve for 120 min was calculated, based on which the percentage inhibition was obtained for each treatment.

Results:

| Group | % change in AUC glucose |
|---|---|
| Vehicle control | — |
| ($SB_{II}$) (10 mg/kg) | −45.7 ± 1.5 |
| (SB) (10 mg/kg) | −36.5 ± 1.6 |
| (SG) (10 mg/kg) | −39.4 ± 1.8 |
| (SBa) (10 mg/kg) | −43.3 ± 1.6 |
| (SP) (10 mg/kg) | −31.9 ± 1.8 |

The results indicate that crystalline besylate salt(II) of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine ($SB_{II}$) and amorphous besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (SBa) are better than crystalline monohydrate form of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate salt (SP) when tested in the acute oral glucose tolerance test in C57 mice.

Therefore, the present (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate, the crystalline form II and amorphous forms of besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine have potentially significant therapeutic advantages compared to the (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (SB) from which it is derived and also better than marketed crystalline monohydrate form of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine phosphate salt (SP).

The invention is further exemplified by the following non-limiting examples, which are illustrative representing the preferred modes of carrying out the invention. The invention's scope is not limited to these specific embodiments only but should be read in conjunction with what is disclosed anywhere else in the specification together with those information and knowledge which are within the general understanding of a person skilled in the art.

Example 1

Preparation of adipic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a 25 mL three neck flask ethanol (10.0 mL) and, (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g) were taken. It was heated to 68-70° C. and adipic acid (0.717 g) was added. The reaction mixture was stirred for 2 hrs at 78-80° C., gradually cooled to 25-30° C.

and again stirred for 2 to 3 hrs. Solid salt precipitated out. The salt was filtered and washed with ethanol which provided the adipic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt.: 1.54 g, % Yield: 56.8%, Purity by HPLC: 99.29%, % chiral purity by HPLC of R-isomer 100.0%), m.p.: 138-142° C., XRD: crystalline—FIG. (3)

Example 2

Preparation of gentisic acid salt (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine and its amorphous form In a 25 mL round bottom flask water (10 mL) and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g) were taken. The reaction mixture was heated up to 98-100° C. to obtain clear solution. To this clear solution gentisic acid (0.756 g) was added and stirred at 98-100° C. for 1 to 2 hrs. The solvent was distilled out at reduced pressure to obtain a solid mass. (Wt.: 2.7 g).

The solid was taken into DIPE (20 mL) and stirred for 1 hr then solvent decanted. Solid was then dissolved into IPA. The solvent was distilled out to obtain the gentisic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine as an amorphous solid. (Wt.: 1.91 g, % purity: 93.47%. % water: 3.99% w/w, XRD=amorphous FIG. (2).

Example 3

Preparation of an amorphous form of gentisic acid salt (2R)-4-oxo-4-[3-(trifluoromethyl)-5,6-dihydro [1,2,4]triazolo[4,3-a]pyrazin-7(8H)-yl]-1-(2,4,5-trifluorophenyl)butan-2-amine In a dry, 50 mL round bottom flask methanol (20 mL) and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (4.0 g) were taken. To this clear solution gentisic acid (1.51 g) was added The reaction mixture was heated up to 65-67° C. and stirred for 2 hrs. The solvent was distilled out at reduced pressure to obtain a solid mass. (Wt.: 5.5 g).

% water: 0.82, XRD: Amorphous FIG. (2). % Purity—99.34%, TGA—4.4%, DSC—87.3 and 213.2

Example 4

Preparation of an amorphous form of gentisic acid salt (2R)-4-oxo-4-[3-(trifluoromethyl)-5,6-dihydro [1,2,4]triazolo[4,3-a]pyrazin-7(8H)-yl]-1-(2,4,5-trifluorophenyl)butan-2-amine The gentisic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was formed by mixing gentisic acid (0.189 g) and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (0.500 g) in methanol (2.5 mL), followed by stirring, at reflux temperature for 2 h. The solvent was distilled out at reduced pressure to obtain solid gentisate salt (Wt.: 0.680 g)

The salt (0.600 g) was dissolved into IPA (1.2 mL). To the solution DIPE (2.4 mL) was added. It was stirred for 1 h at 25-30° C., solid was precipitated then solvent decanted. The residual solvent was distilled out under reduced pressure to obtain the gentisic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine as an amorphous solid. (Wt.: 0.260 g, % purity: 99%, % water: 1.99% w/w, XRD=amorphous FIG. (2).

Example 5

Preparation of an amorphous form of gentisic acid salt (2R)-4-oxo-4-[3-(trifluoromethyl)-5,6-dihydro [1,2,4]triazolo[4,3-a]pyrazin-7(8H)-yl]-1-(2,4,5-trifluorophenyl)butan-2-amine The gentisic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was formed by mixing gentisic acid (0.113 g), (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (0.300 g) in a mixture of isopropylalcohol (0.6 mL) and chloroform (1.5 mL), followed by stirring at reflux temperature for 2 h. The solvent was distilled out at reduced pressure to obtain solid gentisate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine as an amorphous solid. [Wt.: 0.410 g, % purity: 98.9%, XRD=amorphous FIG. (2)].

Example 6

Preparation of an amorphous form of gentisic acid salt (2R)-4-oxo-4-[3-(trifluoromethyl)-5,6-dihydro [1,2,4]triazolo[4,3-a]pyrazin-7(8H)-yl]-1-(2,4,5-trifluorophenyl)butan-2-amine The gentisic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was formed by mixing gentisic acid (0.113 g), (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (0.300 g) in a mixture of isopropylalcohol (0.6 mL) and acetonitrile (1.5 mL), followed by stirring at reflux temperature for 2 h. The solvent was distilled out at reduced pressure to obtain solid gentisate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine as an amorphous solid. [Wt.: 0.410 g, % purity: 98.9%, XRD=amorphous FIG. (2)].

Example 7

Preparation of crystalline form of gentisic acid salt (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a dry, 25 mL round bottom flask methanol (10 mL) and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g) were taken. To this clear solution gentisic acid (0.756 g) was added The reaction mixture was heated up to 65-67° C. and stirred for 2 hrs. The solvent was distilled out at reduced pressure to obtain the gentisic acid salt. The gentisic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (450 mg) was dissolved in ethanol (4.5 mL) and toluene (4.5 mL) was added subsequently, stirred for 2 to 3 hrs. Solid salt was precipitated out, filtered and washed with toluene. Subsequently, solid was dried to obtain the gentisic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine. (Wt.: 257 mg, XRD: crystalline—FIG. (1))

Example 8

Preparation of hydrochloride salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a dry, 50 mL three neck flask methanol (2.5 mL), IPA (21.3 mL) and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2.0 g) were taken. The reaction mixture was heated up to 40-45° C. to obtain clear solution. To this clear solution IPA-HCl was added up to acidic pH and then (2.5 mL) diethyl ether was added into the reaction mixture. It was stirred for 1 hr at 25-30° C. Solid salt was precipitated out. It was then heated up to 55° C. and then cooled to 25-30° C. The solid salt was filtered and washed with IPA. The hydrochloride salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt. 1.1 g, % Purity by HPLC: 99.98%, % chiral purity by HPLC: >99%, m.p.=168-170° C., XRD=crystal line (FIG. 4).

Example 9

Preparation of besylate salt(I) of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a dry, 50 mL round bottom flask isopropyl acetate (25 mL) and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (0.5 g) were taken. The reaction mixture was heated up to 45-50° C. and a solution of benzenesulfonic acid (0.194 g) in (2.3 mL) IPAc was added. Upon complete addition, solid salt was precipitated out. It was then cooled to 25-30° C. The salt was filtered and washed with hexane. The besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt. 0.63 g, % Purity by HPLC: 99.76%, % chiral purity by HPLC: >99%), m.p.=171-174° C., XRD=crystalline (FIG. 5).

Example 10

Preparation of hydrated besylate salt(II) of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a dry, 50 mL round bottom flask isopropyl acetate (250 mL) and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (5.0 g) were taken. The reaction mixture was heated up to 45-50° C. and a solution of benzenesulfonic acid (1.93 g) in a mixture of water (0.5 mL) and isopropyl acetate (23 mL) was slowly added. It was stirred for 2 h at 50° C. It was then cooled to 25-30° C. The salt was filtered and washed with IPA and Hexane. The besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained. It was dried. (Wt. 6.7 g, % Water—2.96%, % Purity by HPLC: >99.0%, % chiral purity by HPLC: >99%), m.p.=172-174° C., XRD=crystalline (FIG. 7).

Example 11

Preparation of hydrated besylate salt(II) of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a dry, 50 mL round bottom flask chloroform (5 mL) and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (0.5 g) and water (0.5 mL) were taken. The mixture was stirred at 25-30° C. for 5-10 min. and solid benzenesulfonic acid (0.193 g) was added. It was heated to reflux temperature and stirred for 2 h. It was then cooled to 25-30° C. and stirred for 68 h at 25-30° C. The salt was filtered and washed with chloroform. The besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained. It was dried. (Wt. 0.660 g, Water—1.93%, % Purity by HPLC: >99.0%, % chiral purity by HPLC: >99%).

Example 12

Preparation of hydrated besylate salt(II) of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine To the 25 mL round bottom flask isopropyl acetate (5 mL), tetrahydrofuran (0.25 mL), water (0.5 mL) and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (0.5 g) were added. The mixture was stirred at 25-30° C. for 5-10 min. and solid benzenesulfonic acid (0.194 g) was added. It was heated to reflux temperature and stirred for 2 h. It was then cooled to 25-30° C. and stirred for 15-30 min. at 25-30° C. The salt was filtered and washed with isopropyl acetate. The besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained. It was dried. (Wt. 0.680 g, % Water—2.2%, % Purity by HPLC: >99.0%, % chiral purity by HPLC: >99%).

Example 13

Preparation of hydrated besylate salt(II) of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine To the 25 mL round bottom flask isopropyl acetate (5 mL), toluene (0.25 mL), water (0.5 mL) and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (0.5 g) were added. The mixture was stirred at 25-30° C. for 5-10 min. and solid benzenesulfonic acid (0.194 g) was added. It was heated to reflux temperature and stirred for 2 h. It was then cooled to 25-30° C. and stirred for 15-30 min. at 25-30° C. The salt was filtered and washed with isopropyl acetate. The besylate; salt of (2R)-4-oxo-4-[3-(trifluoromethyl)-5,6- dihydro[1,2,4]triazolo[4,3-a]pyrazin-7(8H)-yl]-1-(2,4,5-trifluorophenyl)butan-2-amine was obtained. It was dried. (Wt. 0.660 g, % Water—1.61%, % Purity by HPLC: >99.0%, % chiral purity by HPLC: >99%).

Example 14

Preparation of Trifluoroacetic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a dry, 25 mL round bottom flask isopropanol (15 mL) and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (1.0 g) were taken. The reaction mixture was heated up to 78-80° C. and trifluoroacetic acid (0.28 g) was added. It was stirred for 1.5 h at 80-82° C. It was then cooled to 25-30° C. Then the solvent was evaporated. The salt was dissolved into IPA and precipitated with DIPE. The trifluoroacetic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was filtered and washed with DIPE. It was dried. (Wt. 0.89 g, % Purity by HPLC: >98%, % chiral purity by HPLC: >99%), XRD=crystalline (FIG. 6).

Example 15

Preparation of Trifluoroacetic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine The trifluoroacetic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (6.5 g) was stirred with isopropylacetate (90 mL) for 2 hrs at 25-30° C. The salt was filtered and washed with isopropylacetate. It was dried (Wt. 5.4 g, % Purity by HPLC: >98%, % chiral purity by HPLC: >99%, % water—3.14%).

XRD=crystalline (FIG. 6).

Example 16

Preparation of amorphous benzenesulfonic acid salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine In a dry, 25 mL round bottom flask methanol (2 mL) and (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (1.0 g) were taken. Then benzenesulfonic acid (0.38 g) was added. It was stirred for 3 h at 28° C. Further, dichloromethane (10 mL) was added and the reaction mixture was stirred for 1 h at 28° C. Then the solvent was distilled out at 25-30° C. under reduced pressure. The amorphous besylate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine was obtained (Wt. 1.2 g, % Purity by HPLC: >98%, % chiral purity by HPLC: >99%), XRD=amorphous (FIG. 8).

Example 17

Preparation of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine from Monohydrate phosphate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine Monohydrate phosphate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2 g) and water (10 mL) were taken in a 50 ml three neck flask. To the solution sodium chloride (3.4 g), sodium bicarbonate (0.33 g) in small lots and ethyl acetate (20 mL) were added at 25-30° C. It was stirred for 15-30 min. at 40-42° C. It was transferred into a separating funnel; organic layer was collected. The aqueous layer was extracted twice with ethylacetate (20 mL); organic layer was collected. All the organic layers were combined. The solvent was distilled out at reduced pressure to obtain (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (Wt. 1.8 g, % Water—1.18%, % Purity by HPLC: >99.0%).

Example 18

Preparation of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine from Monohydrate phosphate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine Monohydrate phosphate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (2 g) and water (10 mL) were taken in a 50 ml three neck flask. To the solution sodium chloride (3.4 g), 10% aq. sodium hydroxide (3 mL) and ethyl acetate (20 mL) were added at 25-30° C. It was stirred for 15-30 min. at 25-30° C. It was transferred into a separating funnel; organic layer was collected. The aqueous layer was saturated with sodium chloride (3.4 g) and extracted twice with ethylacetate (20 mL). All the organic layers were combined and dried over anhydrous sodium sulfate. The solvent was distilled out at reduced pressure to obtain (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (Wt. 1.6 g, % Water—0.39%, % Purity by HPLC: >99.0%).

Example 19

Preparation of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine The (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (21.0 g, Chiral Purity—96.4%, prepared as per method disclosed in patent WO 2010/032264) was dissolved in isopropylalcohol (42.0 mL) at 68-70° C. Then it was cooled to 45-48° C. and n-heptane (168 mL) was added drop by drop over a period of 30-45 min. The solid was precipitated. It was cooled to 25-30° C. and stirred for 1 h. The solid was filtered and washed with a mixture of isopropylalcohol and n-heptane [63 mL (1:4)]. It was dried at reduced pressure to obtain (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine (17.1 g, Purity—99.5%, Chiral Purity—99.5%, % Water—0.16%.

The invention claimed is:

1. The gentisate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine including their polymorphs.

2. Gentisate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine as claimed in claim 1, which is in crystalline form.

3. Crystalline gentisate salt as claimed in claim 2 which is characterized by PXRD pattern with peaks at about 8.0, 13.73, 16.00, 18.66, 22.61, 25.62 and 26.48°+0.2° two-theta (2θ).

4. Gentisate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine as claimed in claim 3, further characterized by a PXRD pattern substantially as depicted in FIG. 1.

5. A process for preparing the gentisate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine as claimed in claim 1 comprising (a) dissolving (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine in a suitable solvent;
(b) thereafter addition of gentisic acid and reacting under suitable conditions;
(c) removing the solvent under suitable conditions to obtain (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate.

6. The process as claimed in claim 5, wherein the suitable solvent used is selected from alcohols, water or suitable mixture thereof.

7. A process for preparing the crystalline form of gentisate salt of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine as claimed in claim 2, comprising (a) crystallization of (2R) 4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate salt in the presence of suitable solvent and optionally further adding suitable anti solvents and
(b) (b) removing the solvent under suitable conditions to obtain the crystalline form of (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine gentisate.

8. The process as claimed in claim 7, wherein the suitable solvent used is selected from hydrocarbons and mixture of alcohols and hydrocarbons.

* * * * *